(12) United States Patent
Müller-Hasky et al.

(10) Patent No.: US 7,977,479 B2
(45) Date of Patent: Jul. 12, 2011

(54) METHOD FOR PRODUCING MELAMINE WITH HEAT RECOVERY

(75) Inventors: Martin Müller-Hasky, Heusenstamm (DE); Jürgen Eberhardt, Rodgau (DE); Arne Schadt, Bad Nauheim (DE)

(73) Assignee: Lurgi AG, Frankfurt am Main (DE)

( * ) Notice: Subject to any disclaimer, the term of this patent is extended or adjusted under 35 U.S.C. 154(b) by 864 days.

(21) Appl. No.: 11/919,609

(22) PCT Filed: Mar. 6, 2006

(86) PCT No.: PCT/EP2006/002019
§ 371 (c)(1),
(2), (4) Date: Oct. 30, 2007

(87) PCT Pub. No.: WO2006/119815
PCT Pub. Date: Nov. 16, 2006

(65) Prior Publication Data
US 2009/0030201 A1   Jan. 29, 2009

(30) Foreign Application Priority Data

May 6, 2005   (DE) .................. 10 2005 021 082
May 13, 2005  (DE) .................. 10 2005 023 041

(51) Int. Cl.
C07D 251/60   (2006.01)
C07D 251/62   (2006.01)
(52) U.S. Cl. ........................................ 544/201; 544/203
(58) Field of Classification Search ............... 544/201, 544/203
See application file for complete search history.

(56) References Cited

U.S. PATENT DOCUMENTS 3,895,007 A * 7/1975 Schwarzmann et al. ...... 544/201
4,348,520 A * 9/1982 Bruls et al. .................... 544/201

OTHER PUBLICATIONS

Crews et al: "Melamine and Guanamines", Ullmann's Encyclopedia of Industrial Chemistry, vol. 21, 2003, pp. 205-216, figures 1-3.
Abstract of CN 000001188761A; Jiang Dazhou; Preparation technology of melamine and its device, Jul. 29, 1998.

* cited by examiner

*Primary Examiner* — Venkataraman Balasubramanian
(74) *Attorney, Agent, or Firm* — Jonathan Myers; Andrew Wilford

(57) ABSTRACT

The invention relates to a method for producing melamine by decomposing urea inside a fluidised bed reactor, during which the hot reaction gas is cooled inside a gas cooler, and the obtained heat is directly used for pre-heating the fluidizing gas required for creating the fluidized bed.

7 Claims, 2 Drawing Sheets

METHOD FOR PRODUCING MELAMINE WITH HEAT RECOVERY

CROSS REFERENCE TO RELATED APPLICATIONS

This application is the US national phase of PCT application PCT/EP2006/002019, filed 6 Mar. 2006, published 16 Nov. 2006 as WO 2006/119815, and claiming the priority of German patent application 102005021082.1 itself filed 6 May 2005 and German patent application 102005023041.5 itself filed 13 May 2005, whose entire disclosures are herewith incorporated by reference.

FIELD OF THE INVENTION

The invention relates to a method of producing melamine by the decomposition of urea in a fluidized-bed reactor, the hot reaction gas being cooled in a gas cooler and the obtained heat being directly used to preheat the fluidizing gas required for producing the fluidized bed.

BACKGROUND OF THE INVENTION

The production of melamine starting from urea is a method that has been known for quite some time, a distinction being drawn between two types of processes: The noncatalytic high-pressure process and the catalytic low-pressure process. The high-pressure process requires pressures of at least 8 MPa, while the catalytic low-pressure process is carried out in a fluidized bed at a pressure of no more than 1 MPa and temperatures of at least 380 to 410° C. The carrier gas used for the low-pressure method comprises either ammonia or a mixture of carbon dioxide and ammonia, the resulting melamine being present in gaseous form after the reaction.

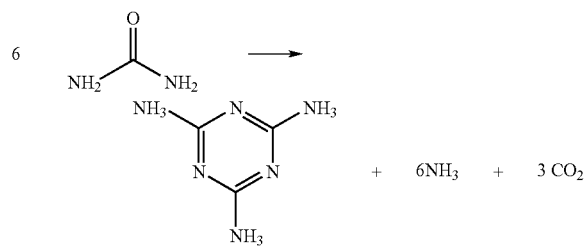

The reaction of urea to form melamine is endothermic, so that the system must be provided with large amounts of external heat.

The yield of melamine with this method in relation to the quantity of urea used is 90 to 95%. In the literature, the three most frequently used low-pressure methods are known as BASF, Chemie Linz and Stamicarbon processes.

The BASF process is a single-stage reaction method (FIG. 1), where liquid urea is reacted in a fluidized bed at a temperature of 395 to 400° C. under nearly atmospheric pressure. In addition to melamine, the resulting reaction gas includes traces of by-products such as melem and melam as well as reaction gas comprising ammonia and carbon dioxide. The reaction gas mixture that is obtained is then cooled, the removed catalyst and the crystallized by-products are separated out and the reaction gas comprising the melamine is fed to a crystallizer. In the crystallizer, the melamine-containing gas is cooled with reaction gas to lower the temperature of the melamine-containing gas to a range of 190 to 210° C. Under these conditions, melamine desublimes approximately 98% from the reaction gas. After separating out the melamine, the remaining gas (recycle gas) is pumped to a urea-washing station by means of a recycle gas blower, where it is cooled and washed in direct contact with the liquid urea. The temperature of the quenching gas is ~138° C., so that it is necessary to admix 2.5 to 3.5 kg of quenching gas per kilogram of melamine-containing gas to get a temperature of 190 to 220° C. in the crystallization apparatus.

The production of melamine is a fully developed process that has been known for a long time. For example, German unexamined patent application DE 33 02 833 [U.S. Pat. No. 3,321,603] describes a method of the catalytic production of melamine by means of thermal conversion of urea. In this method, the synthesis gases from which the melamine has already been deposited are treated with a urea melt, wherein the treatment is performed in a scrubber.

The problems with the known process, however, are that due to the endothermic chemical reaction large amounts of heat are required to maintain the fluidized-bed reactor at the required reaction temperature of 395 to 400° C., and additionally that cooling of the melamine-containing reaction gas exiting the fluidized-bed reactor is essential to precipitate undesirable by-products, such as melem or melam. Cooling the gas comprising melamine creates some difficulty. The start of the desublimation process is dependent on the pressure and content of melamine in the gas exiting the reactor. Once the partial pressure reaches the is saturation vapor pressure of melamine, the melamine will crystallize. It is therefore essential that the cooler downstream of the reactor does not cool the gas too much, which would bring about the desublimation process already there. It must also be ensured that in the cooler itself no locations (meaning pipe walls) are below the desublimation temperature because otherwise melamine would crystallize. These melamine adhesions result in drastically shortened plant operating life, undesirable production failure and an increased need for maintenance. To prevent this type of adhesion, heat is removed with the help of a special heat transmission medium (thermal oil) that operates at a temperature at which the critical pipe wall temperature of the cooler does not drop below the melamine desublimation temperature. The thermal oils are higher molecular hydrocarbons (for example phenyls, derivatives thereof and mixtures thereof), which upon release may have severe impact on humans and the environment as well as objects (toxic, flammable). The thermal oil in turn must be treated in a downstream cooler or condenser.

OBJECT OF THE INVENTION

It is therefore the object of the present invention to provide a method that makes it possible to maintain the required reaction temperature of 395 to 400° C. in the fluidized-bed reactor in a cost-efficient and therefore economical manner and at the same time remove the reaction heat from the melamine-containing reaction gas, without utilizing any heat transmission medium that may have critical properties. At the same time, the critical pipe wall temperature is to be adjusted such that undesirable premature desublimation of melamine in the cooler is prevented.

SUMMARY OF THE INVENTION

This object is achieved by the inventive method of producing melamine by the decomposition of urea inside a fluidized-bed reactor, in that the hot reaction gas is cooled in a gas cooler and the thus-obtained heat is directly transmitted to preheat the fluidizing gas required for producing the fluidized bed. This solution was found by using the gas that is required for fluidizing the fluidized bed directly as a cooling agent in the cooler downstream of the reactor.

The advantages achieved by the invention are that the inventive method enables the temperature of the melamine-containing reaction gas to be lowered to a level that allows separation of undesirable by-products, such as melem and melam. At the same time, the amount of heat that is obtained is used to heat the fluidizing gas. The inventive method makes it possible to economically recover a portion of the required reaction heat and forego the use of an additional heat transmission medium as well as the associated equipment (pumps, reservoir, condenser or cooler). Furthermore, considerable amounts of primary fuel can be saved because the amount of heat required to cover the endothermic reaction can be reduced considerably.

Advantageous embodiments of the invention are now detailed. According to the present invention, it is possible to cool the reaction gases in the gas cooler from a range of 380 to 420° C. to a range of 210 to 300° C. According to the present invention, it is furthermore possible to perform the heat transmission in a tubular or plate-shaped heat exchanger. According to a further embodiment of the present invention, the media in the heat exchanger streams are either in parallel-flow or counter-flow. According to another feature of the present invention, it is possible to use a by-pass for regulating the temperature.

BRIEF DESCRIPTION OF THE DRAWINGS

Illustrated embodiments of the invention are illustrated in the drawings and described in detail hereinafter. Therein.

DETAILED DESCRIPTION OF THE DRAWINGS

Figure 1:
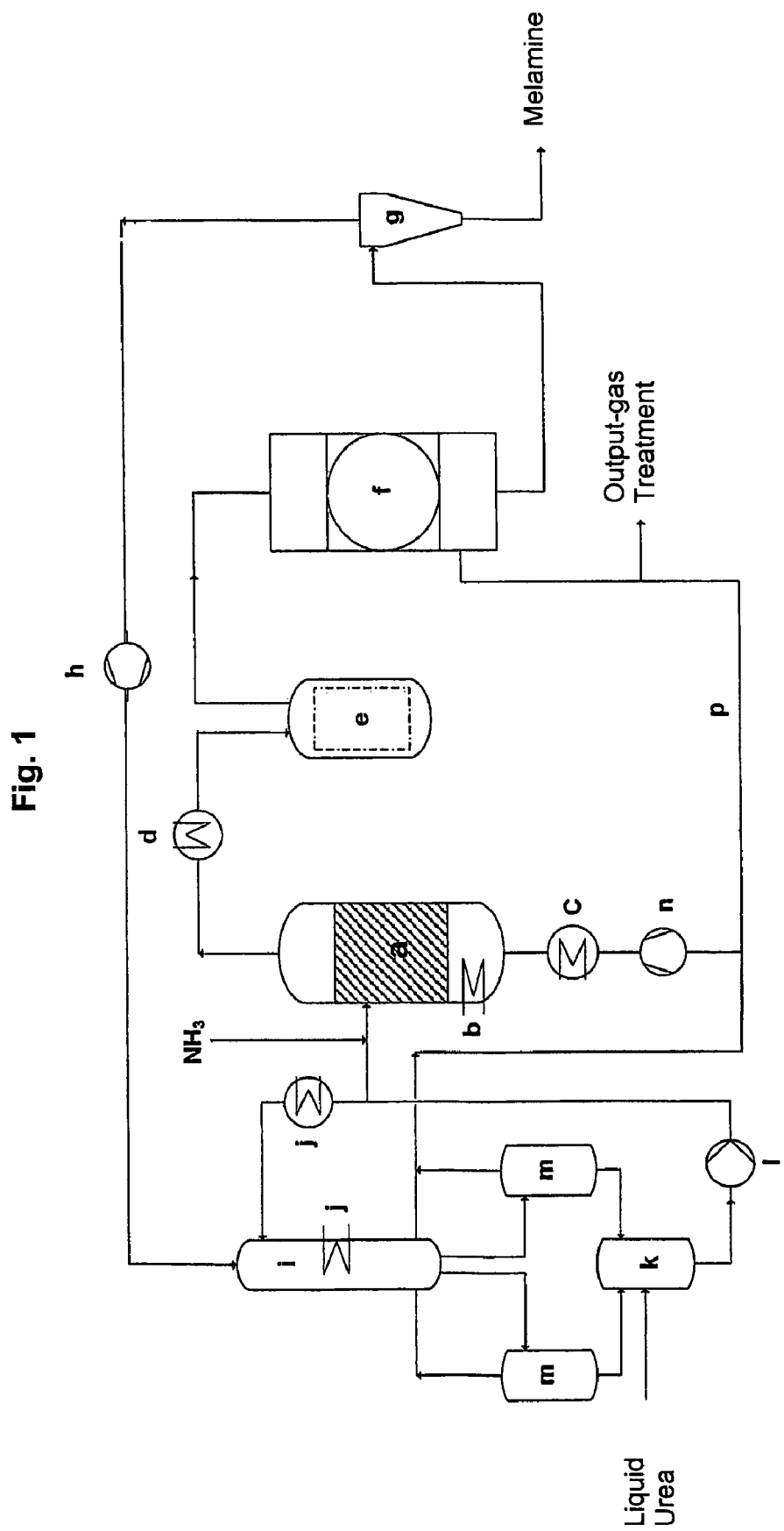
FIG. 1 shows a method of producing melamine according to the BASF process.

FIG. 1 shows the method of producing melamine according to the BASF process. Liquid urea is fed to the system from a urea reservoir k. A pump l is used to feed urea to the urea-washing station i; the liquid and gaseous components are separated from each other in a downstream mist collector m. A portion of the resulting gaseous components is compressed by a compressor n, preheated in a heater c and then fed to a reactor a where the components are required to form the catalytically effective fluidized bed. The gaseous components exiting the reactor a are cooled by a gas cooler d and then fed to a gas filter e. Precipitated by-products, such as melem, melam and catalyst discharge, are separated from the reaction gas in this gas filter e. The resulting reaction gas is then supplied to a crystallization device f where the gas is cooled with other reaction gas (quenching gas), which preferably has a temperature of approximately 140° C., to a temperature ranging between 190 and 210° C. The crystalline melamine obtained in the crystallization device is then supplied to a product cyclone g where the gaseous phase is separated from crystalline melamine. After separating the melamine, the gas is pumped to the urea-washing station i by means of a recycle gas blower h.

Figure 2:
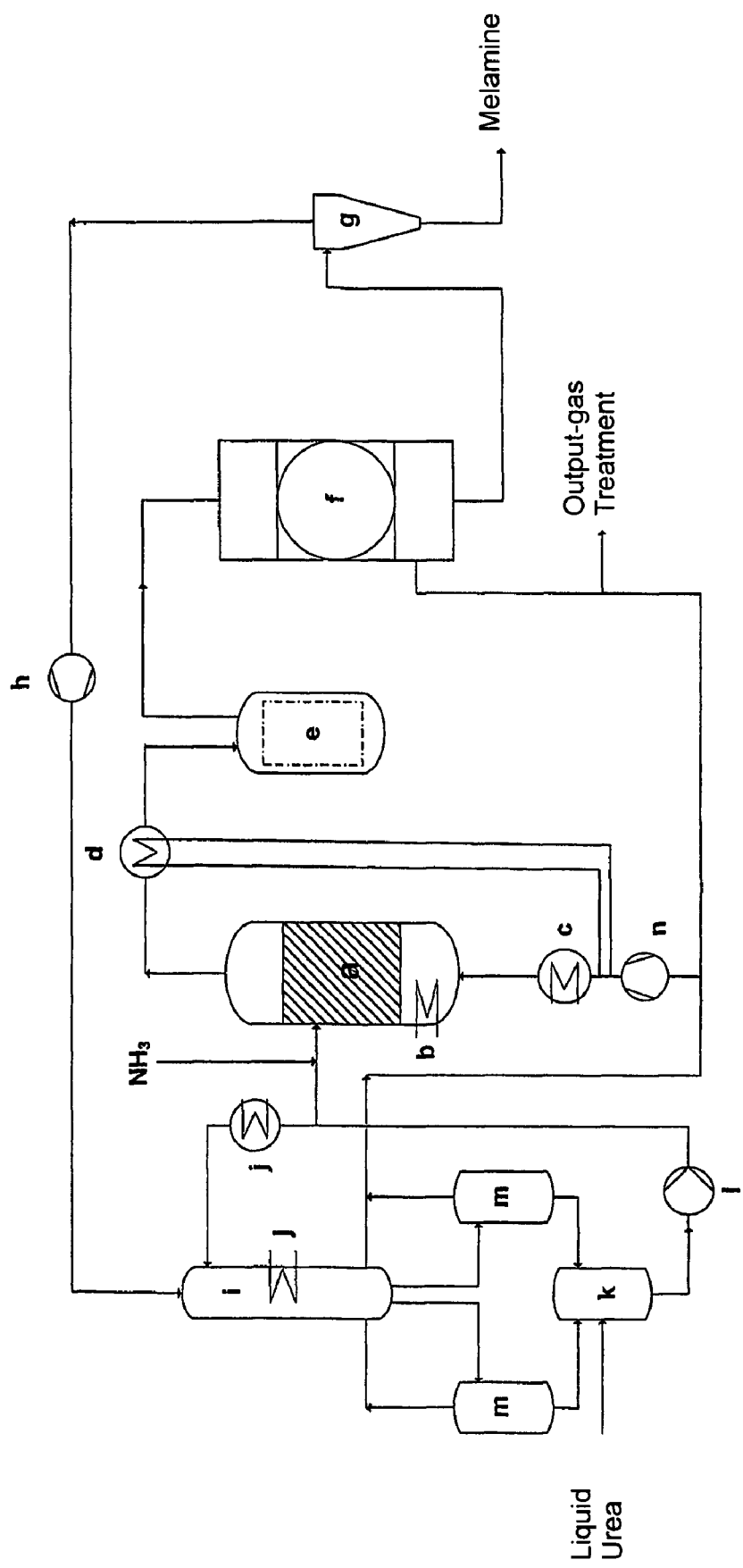
FIG. 2 shows a method according to the invention for producing melamine with heat recovery.

FIG. 2 shows a method according to the invention for producing melamine with heat recovery. Liquid urea is fed to the system by means of a urea reservoir k. Liquid urea is supplied to the urea-washing station i by means of a pump l and cooling unit j, where subsequently liquid and gaseous components are separated from each other in a mist collector m. The gaseous components are then compressed by a compressor n. The compressed gas required for forming the catalytically acting fluidized bed is preheated with the hot reaction gas from the reactor in a gas cooler d. The compressed gas cools the hot reaction gas containing melamine coming from the reactor. Thereafter, the preheated fluidizing gas flows through another gas heater c to heat the gas approximately to the temperature of 400° C.; the heated gases are then returned to the reactor a. After being cooled in the gas cooler d, the gaseous components formed in the reactor are fed to a gas filter e in which crystallized components such as melem, melam and catalyst discharge are separated from the gaseous components. Then, the reaction gases are introduced into a crystallization device f, where the gas is cooled with other reaction gases (quenching gas), which preferably have a temperature of approximately 140° C., to a temperature ranging between 190 and 210° C. The formed melamine is then separated from the gaseous components by a product cyclone g. The gas flows back to the urea-washing station with the help of the recycle gas blower h. There, the gases are cooled and washed with liquid urea.

The invention will be explained in more detail with the examples 1 and 2.

Example 1

Example 1 describes the conventional cooling process of gas with evaporating thermal oil. The hot, melamine-containing gas stream exiting the reactor a has a temperature of 400° C. and a pressure of 0.17 MPa (abs.) and the following composition.

|  | kmol/h | mole % |
|---|---|---|
| Ammonia $NH_3$ | 1709 | 67 |
| Carbon Dioxide $CO_2$ | 740 | 29 |
| Melamine $C_3H_6N_6$ | 51 | 2 |
| Is cyanic Acid HNCO | 38 | 1.5 |
| Inert | 31 | 0.5 |
| Total | 2551 | 100 |

The partial pressure of melamine is consequently 0.0034 MPa. The saturation temperature at this pressure level is approximately 310° C. Consequently, the gas in the downstream cooler d must not be cooler than 310° C. or must not drop below the temperature of 310° C. anywhere in the cooler because otherwise melamine would crystallize. The evaporating thermal oil is conducted on the outer side of a tubular heat exchanger. Due to the extremely high heat transmission on the outer side, the inside wall temperature of the pipes will take on approximately the same temperature as that of the evaporating thermal oil. Consequently, the evaporation temperature of the thermal oil must be adjusted to at least 315° C. The thermal conductivity coefficient (k-value) on the other hand, which together with the logarithmic mean temperature difference defines the surface of a heat exchanger, will always be smaller than the smallest heat transfer coefficient (alpha-value). The smallest alpha value will be on the side of pipe through which gas flows and, based on experience, is very small. For example, in this example it is approximately 160 W/m²C. The gas that comes from the reactor is cooled in the cooler to approximately 340° C. As a result, a logarithmic mean temperature difference of approximately 40° C. exists between the gas and the thermal oil.

Example 2

The gas from the reactor a in the same composition and with the same pressure and temperature as in Example 1 is cooled in a downstream cooler to 340° C. The cooling-medium used is the gas that is required for fluidizing the fluidized bed. For this purpose, the gas coming from the compressor is guided on the jacket side of a tubular heat exchange. The compressed gas will heat from approximately 240° C. to 315° C. The thermal conductivity coefficient (k-value) will take on a value of approximately 160 W/m²° C., as in Example 1. When the hot and cold gases are routed in parallel flow through the heat exchanger, the lowest inside wall temperature of the pipe will be 315° C. This safely prevents premature and undesirable desublimation of melamine. The resulting logarithmic mean temperature difference is approximately 73° C. For the same amount of heat to be removed as in Example 1, a heat exchanger with a surface smaller by a factor of 1.8 is required. As a result, less heat is supplied to the system from the outside. The amount of heat saved of approximately 1,800 kW corresponds to annual savings of approximately 130,000 euros (at an operating time of 8,000 hours annually and 2.5 euros per GJ fuel) or a savings of approximately 12% of primary fuel.

LIST OF REFERENCE NUMERALS a) Fluidized-bed reactor
b) Heater
c) Gas heater
d) Gas cooler
e) Gas filter
f) Crystallization device
g) Product cyclone
h) Recycle gas blower
i) Urea washing station
j) Cooling unit
k) Urea reservoir
l) Pump
m) Mist collector
n) Compressor

The invention claimed is:

1. A process for producing melamine from urea, which comprises the steps of:
   (a) feeding a fluidizing gas to a catalytically activated, fluidized bed reactor to create a fluidized bed within the fluidized bed reactor;
   (b) feeding liquid urea to the fluidized bed of the catalytically activated fluidized bed reactor, said fluidized bed externally heated to a temperature of 380 to 410° C. to decompose the liquid urea into a hot reaction gas containing melamine, ammonia and carbon dioxide; and
   (c) removing the hot reaction gas from the fluidized bed reactor, and cooling the hot reaction gas in a cooler in heat exchange with the fluidizing gas, prior to introducing the fluidizing gas into the fluidized bed of the catalytically activated, fluidized bed reactor according to step (a), to extract heat from the hot reaction gas and directly transmit the extracted heat to the fluidizing gas to preheat the fluidizing gas required according to step (a), thereby reducing the need to apply external heat to the fluidized bed reactor according to step (b).

2. The process for producing melamine from urea according to claim 1, step (c), wherein the temperature of the hot reaction gas removed from the fluidized bed reactor is lowered to 210 to 300° C. following the heat exchange with the fluidizing gas.

3. The process for producing melamine from urea according to claim 1, step (c), wherein the fluidizing gas used to cool the hot reaction gas has a temperature of about 140° C.

4. The process for producing melamine from urea according to claim 1, step (c), wherein the cooler is a tubular heat exchanger or a plate-shaped heat exchanger.

5. The process for producing melamine from urea according to claim 1, step (c), wherein the hot reaction gas and the fluidizing gas pass through the cooler in parallel-flow or counter-flow.

6. The process for producing melamine from urea according to claim 1, wherein following step (c), the fluidizing gas is further preheated to a temperature of 400° C. before being fed to the fluidized bed of the catalytically activated fluidized bed reactor according to step (a).

7. The process for producing melamine from urea according to claim 1, wherein following step (c), the process further comprises the following steps:
   (d) filtering the hot reaction gas to remove crystallized melem and melam, and catalyst discharge;
   (e) further cooling the hot reaction gas to a temperature of 190° to 210° C. to crystallize melamine; and
   (f) separating the melamine from the hot reaction gas.

* * * * *